United States Patent [19]

Sondermeijer et al.

[11] Patent Number: 5,187,087
[45] Date of Patent: Feb. 16, 1993

[54] RECOMBINANT HERPESVIRUS OF TURKEYS AND LIVE VECTOR VACCINES DERIVED THEREOF

[75] Inventors: Pulus J. A. Sondermeijer; Johannes A. Claessens, both of Boxmeer, Netherlands; Albert P. A. Mockett, Huntington Cames, United Kingdom

[73] Assignee: AKZO N.V., Arnhem, Netherlands

[21] Appl. No.: 621,193

[22] Filed: Nov. 30, 1990

[30] Foreign Application Priority Data

Dec. 4, 1989 [EP] European Pat. Off. ..... 89.2003071.9

[51] Int. Cl.⁵ .................. C12N 15/00; C12N 7/00; C12N 5/00; C07H 15/12
[52] U.S. Cl. ................... 435/172.1; 435/235.1; 435/172.3; 435/240.2; 435/320.1; 536/23.72; 424/85.8; 424/88
[58] Field of Search ............ 435/68, 70.1, 235.1, 435/236, 237, 320.1, 173.1, 172.1, 240.2; 536/27; 424/85.8

[56] References Cited

U.S. PATENT DOCUMENTS 4,859,587  8/1989  Roizman .................. 435/68

FOREIGN PATENT DOCUMENTS 0334530  9/1989  European Pat. Off. .
90291277  9/1988  Japan ...................... 15/83

OTHER PUBLICATIONS

Igarashi et al. (1987), vol. 157, pp. 351-358.

Primary Examiner—David L. Lacey
Assistant Examiner—Gian P. Wang
Attorney, Agent, or Firm—Donna Bobwicz

[57] ABSTRACT

The present invention is concerned with a recombinant Herpesvirus of Turkeys (HVT), containing a heterologus gene incorporated into an insertion-region of the genome of HVT. The invention also relates to a vector vaccine comprising such a recombinant HVT which expresses a heterologous antigenic polypeptide and induces an adequate immune response on infection of an appropriate host animal.

19 Claims, 6 Drawing Sheets

/////  HVT HOMOLOGOUS REGION

////// HVT HOMOLOGOUS REGION

////// HVT HOMOLOGOUS REGION

RECOMBINANT HERPESVIRUS OF TURKEYS AND LIVE VECTOR VACCINES DERIVED THEREOF

BACKGROUND OF THE INVENTION

The present invention is concerned with a recombinant Herpesvirus of Turkeys (HVT) containing a heterologous, nucleic acid sequence introduced into an insertion region of the HVT genome, a nucleic acid sequence comprising a heterologous gene flanked by DNA sequences derived from said insertion region of the HVT genome, a plasmid comprising said nucleic acid sequence, a process for the preparation of a recombinant HVT, a cell culture infected with a recombinant HVT, a vaccine comprising recombinant HVT as well as a process for the preparation of such a vaccine and antiserum comprising antibodies directed against a recombinant HVT.

Marek's disease (MD) is an oncogenic lymphoproliferative disorder of chickens which results in T-cell lymphomas and peripheral nerve demyelination and is a major cause of economic loss to the poultry industry.

Marek's disease virus (MDV) has been identified as the etiologic agent of MD.

A prototype MD vaccine consists of Herpesvirus of Turkeys (HVT), a serotype 3 MD virus originally isolated from turkeys. Its lack of pathogenicity, oncogenicity, its good replication in vivo and in vitro, availability as cell-free and cell-associated preparations and high protective efficacy have established HVT as a very successful and widely used safe vaccine for the effective control of Marek's disease in poultry.

At present, in general, animals can be protected against infection of pathogenic micro-organisms with live or inactivated vaccines or by vaccines derived from subunits of the relevant pathogens.

However, these types of vaccines may suffer from a number of drawbacks. Using attenuated live viral vaccines always involves the risk of inoculating animals with inadequately attenuated pathogenic micro-organisms. In addition the attenuated viruses may revert to a virulent state resulting in disease of the inoculated animals and the possible spread of the pathogen to other animals.

Inactivated vaccines generally induce only a low level of immunity, requiring additional immunizations. Furthermore, the neutralization inducing antigenic determinants of the viruses may become altered by the inactivation treatment, decreasing the protective potency of the vaccine.

Moreover, a problem with combined live viral vaccines is the mutual influence of the antigenic components resulting in a decrease of the potency of one or more of the constituting components.

A recombinant or naturally derived subunit vaccine also displays a number of disadvantages. First, a polypeptide subunit presented to the immune system as a non-replicating structure often does not elicit long-lasting immunity requiring also the presence of an adjuvant. Secondly, a presentation as a replicating structure can elicit immunity more efficiently than can a presentation as a subunit structure.

BRIEF DESCRIPTION OF THE INVENTION

It is an object of the present invention to provide a recombinant HVT which can be used not only for the preparation of a vaccine against MD but also against other infectious diseases of poultry, which obviates any potential risk associated with the use of a live attenuated pathogen as a vaccine, which stimulates both the humoral and cellular immune system in a potent way without the explicit need of an adjuvant and which offers the possibility of a multivalent vaccine without the risk of adverse mutual interference of different antigenic components.

According to the present invention such a recombinant HVT is characterized in that it contains a heterologous nucleic acid sequence encoding a polypeptide heterologous to HVT, said nucleic acid sequence being introduced in an insertion region of the HVT genome which corresponds with the genomic region from the end of ORF-1 up to and including ORF-5 as shown in FIG. 1 and located within a DNA fragment of the HVT genome having a restriction enzyme map essentially defined by FIG. 1.

BRIEF DESCRIPTION OF THE FIGURES

FIG. 2 B is a restriction map of pMD12gal.

FIG. 3 B is a restriction map of pMD44.

FIG. 6 B is a restriction map of pNDVO5.

DETAILED DESCRIPTION OF THE INVENTION

The recombinant HVT according to the invention can be derived from any HVT strain, e.g. PB-THV1 (commercially available from Intervet International) or strain FC126.

The term "recombinant HVT" as used herein denotes infective virus which has been genetically modified by the incorporation into the virus genome of a heterologous nucleic acid sequence, i.e. DNA which codes for a gene or part thereof not identical to the nucleic acid sequence of a gene naturally present in HVT.

On infection of a cell by the recombinant HVT, the recombinant HVT expresses the heterologous gene in the form of a heterologous polypeptide.

The term "polypeptide" refers to a molecular chain of amino acids with a biological activity, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

The prerequisite for a useful recombinant HVT is that the heterologous nucleic acid sequence is incorporated in a permissive position or region of the genomic HVT sequence, i.e. a position or region which can be used for the incorporation of a heterologous sequence without disrupting essential functions of HVT such as those necessary for infection or replication. Such a region is called an insertion region.

The insertion region refered to in the present invention has not been previously described for the incorporation of heterologous DNA without disrupting essential functions of HVT. Moreover, no information has been available with regard to the restriction enzyme map of the genomic region of HVT used to incorporate a heterologous DNA sequence as described herein.

The insertion region used to incorporate a heterologous DNA sequence in order to prepare a recombinant HVT according to the invention is located within a 17.5 kb restriction fragment generated by partial digestion of genomic HVT DNA with the enzyme Sau3A.

Said fragment is analyzed in detail by restriction enzyme ma 1) and essentially corresponds to of the Unique short ("US") region of the HVT genome, probably including flanking parts of the short internal repeat "IRs") and short terminal repeat ("TRs") structures. The relative positions of the Us region and the IRs and TRs structures within the HVT genome are shown by Igarashi et al. (1987).

Figure 1:
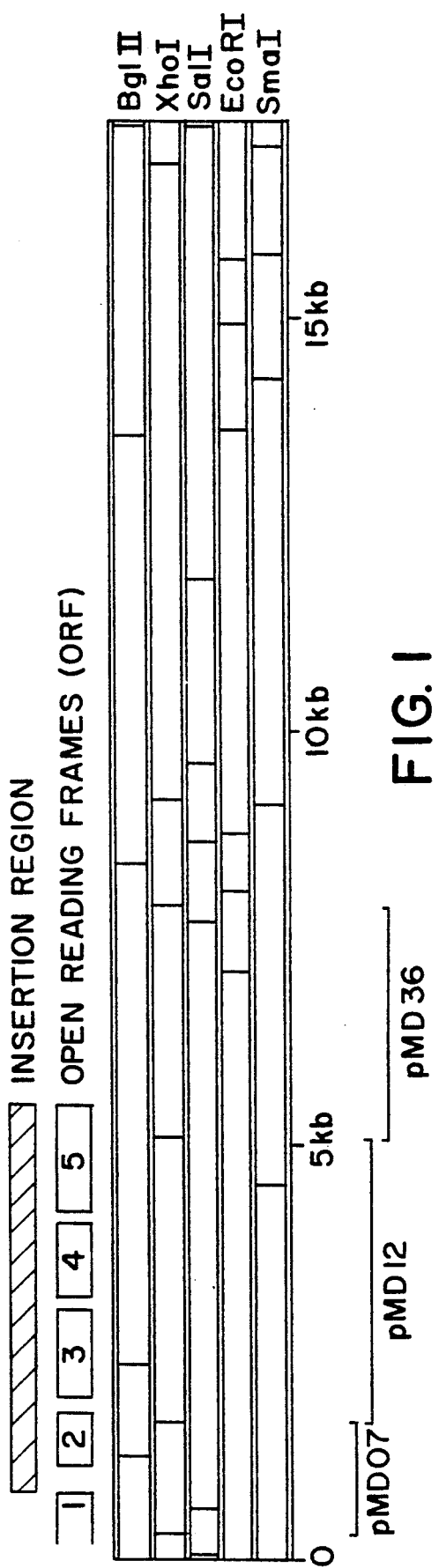
FIG. 1 is a restriction enzyme map of a DNA fragment essentially corresponding to the Us region of the HVT genome.

The insertion region disclosed herein is located within three contiguous XhoI fragments of about 1.2 kb, 3.5 kb and 2.8 kb respectively, and begins at the end of an open reading frame (ORF-1) starting at a position in the HVT genome leftwards of the 1.2 kb XhoI fragment (FIG. 1). Said insertion region of about 5 kb continues through the ORF's, 2, 3, 4 and 5 including the non-coding sequences in between. DNA sequences corresponding to the insertion region outlined above can be applied for the insertion of genes into the HVT genome without disrupting essential functions of the virus.

Particularly, ORF-2 and ORF-3 can be applied for the integration of foreign genes.

Preferred insertion sites for foreign genes within ORF-2 and ORF-3 are the unique BglII restriction sites shown in FIG. 1.

The β-galactosidase gene is inserted at either of the unique BglII restriction sites within ORF-2 and ORF-3 resulting in a recombinant virus which is viable and stable and not only replicates in tissue culture but also infects chickens to a comparable extent as the HVT virus from which it has been derived. E. coli transformed with plasmids designated pMD07gal or pMD12gal (FIG. 2), derived by insertion of the B-gal gene into the unique BglII site of pMD07 and pMD12 which carry the respective XhoI fragments as indicated in FIG. 1, are deposited at the C.N.C.M. of the Institute Pasteur at Paris under accession number I-914 and I-915.

In another example significant parts of the ORF-4 and ORF-5 have been deleted from the HVT genome and replaced by the β-galactosidase marker gene resulting in recombinant viruses comparable with recombinant HVT viruses comprising an insertion of the marker gene in ORF-2 or ORF-3.

It will be understood that for the DNA sequence of the HVT genome, natural variations can exist between individual HVT viruses. These variations may result in deletions, substitutions, insertions, inversions or additions of one or more nucleotides which possibly influence the position of one or more restriction sites, thus affecting the restriction enzyme map shown in FIG. 1.

Moreover, the potential exists to use genetic engineering technology to bring about above mentioned variations resulting in a DNA sequence with a restriction enzyme map related to the map shown in FIG. 1. It is clear that a recombinant HVT comprising a heterologous gene incorporated into an insertion region located within the HVT genomic region characterized by such a related restriction enzyme map is also included within the scope of the present invention. Furthermore, as the insertion region identified according to the present invention does not display essential functions, said region can be deleted partially or completely, whereafter a heterologous gene can be incorporated into said deletion. It will be understood that a recombinant HVT comprising a heterologous gene incorporated into a region of the HVT genome corresponding to the insertion region of the present invention and characterized herein also forms part of the invention.

In summary, the insertion region essentially defined above characterizes the localization of a region within the HVT genome which can be used to incorporate a heterologous nucleic acid sequence.

It is a preferred object of the present invention to provide a recombinant HVT that contains a heterologous nucleic acid sequence which is incorporated into an insertion region essentially characterized by the HVT DNA sequence as shown in SEQ ID NO: 1, containing four ORF's. ORF-2, small open reading frame of 209 amino acids (SEQ ID NO: 2) is located between nucleotide positions 316 and 945 and contains the BglII restriction site from pMD07 used for the insertion of genes into the HVT genome (FIG. 1, SEQ ID NO: 1), thereby indicating that the hypothetical polypeptide encoded for by ORF-2 does not have an essential function for maintenance of the virus in vivo or in vitro. This also applies for ORF-3, comprising 346 amino acids (SEQ ID NO: 3), which is translated in the reverse orientation between nucleotide positions 1084 and 2124 (complementary), and contains the BglII restriction site which is used in pMD12 for the insertion of genes into the HVT genome (FIG. 1, SEQ ID NO: 1). ORF-4 is transcribed towards the $IR_S$ between nucleotide positions 2322 and 3170 (complementary, Figure SEQ ID NO: 1) and encodes 282 amino acids (SEQ ID NO: 4) while ORF-5 starts at nucleotide position 3320 and continues up to nucleotide position 4504 (FIG. 1, SEQ ID NO: 1) encoding a polypeptide of 394 amino acids (SEQ ID NO: 5).

According to the invention a continuous DNA stretch of the HVT genome of about 5 kb starting after the end of ORF-1 at nucleotide position 82 essentially characterized by the DNA sequence shown in SEQ ID NO: 1, comprising four open reading frames and noncoding sequences in between, can be applied for the insertion of heterologous genes into the HVT genome without disrupting essential functions of the virus.

Particularly, the DNA stretches between nucleotide positions 316-945, 1084-2124, 2322-3170 and 3320-4504 shown in SEQ ID NO: 1 have been defined for the integration of foreign genes, the unique BglII restriction sites being the most favoured sites for insertion.

It is clear that for the DNA sequence shown in SEQ ID NO: 1, characterizing the insertion region according to the present invention, natural variations exist between individual HVT viruses resulting in deletions, substitutions, insertions, inversions etc. of one or more nucleotides. These variations can also be brought about by genetic engineering. Recombinant HVT comprising a heterologous gene incorporated into such a region of the HVT genome related but not identical to the insertion region characterized above, also is included within the present invention. For example a heterologous gene can be incorporated into a deletion brought about in the nucleic acid sequence of the HVT genome shown in SEQ ID NO: 1. The HVT insertion-region defined herein by the DNA sequence shown in SEQ ID NO: 1 characterizes the localization of a region within the HVT genome which can be used to incorporate a heterologous nucleic acid sequence.

The heterologous nucleic acid sequence to be incorporated into the HVT genome according to the present invention can be derived from any source, e.g. viral, prokaryotic, eukaryotic or synthetic. Said nucleic acid sequence can be derived from a pathogen, preferably an avian pathogen, which after insertion into the HVT genome can be applied to induce immunity against disease. Preferably, nucleic acid sequences derived from Infectious Bronchitis Virus (IBV), Marek's Disease Virus (MDV), Newcastle Disease Virus (NDV), Infectious Bursal Disease Virus (IBDV), Chicken Anemia Agent (CAA), Reovirus, Avian Retro Virus, Fowl Adeno virus, Turkey Rhinotracheitis Virus, Eimeria species, Salmonella species, Escherichia coli and Mycoplasma gallisepticum are contemplated for incorporation into the insertion region of the HVT genome.

Furthermore, nucleic acid sequences encoding polypeptides for pharmaceutical or diagnostic applications, in particular immune modulators such as lymphokines, interferons or cytokines, may be incorporated into said insertion region.

An essential requirement for the expression of the heterologous nucleic acid sequence in a recombinant HVT is an adequate promotor operably linked to the heterologous nucleic acid sequence. It is obvious to those skilled in the art that the choice of a promotor extends to any eukaryotic, prokaryotic or viral promotor capable of directing gene transcription in cells infected by the recombinant HVT, e.g. promotors derived of the retroviral long terminal repeat, SV40 or promotors present in HVT.

The technique of in vivo homologous recombination can be used to introduce the heterologous nucleic acid sequence into the HVT genome. This is accomplished by first constructing a recombinant DNA molecule for recombination with HVT. Such a molecule may be derived from any suitable plasmid, cosmid or phage, plasmids being most preferred, and contains a heterologous nucleic acid sequence, if desired operably linked to a promotor. Said nucleic acid sequence and promotor are introduced into a fragment of genomic HVT DNA containing insertion region, sequences as defined herein subcloned in the recombinant DNA molecule. The insertion region sequences which flank the heterologous nucleic acid sequence should be of appropriate length as to allow in vivo homologous recombination with the viral HVT genome to occur. If desired, a construct can be made which contains two or more different heterologous nucleic acid sequences derived from e.g. the same or different pathogens said sequences being flanked by insertion region sequences of HVT defined herein. Such a recombinant DNA molecule can be employed to produce recombinant HVT which expresses two or more different antigenic polypeptides to provide a multivalent vaccine. Secondly, cells, e.g. chicken embryo fibroblasts (CEF), can be transfected with HVT DNA in the presence of the recombinant DNA molecule containing the heterologous nucleic acid sequence flanked by appropriate HVT sequences whereby recombination occurs between the insertion region sequences in the recombinant DNA molecule and the insertion region sequences in HVT. Recombination can also be brought about by transfecting the infected cells with a nucleic acid sequence containing the heterologous nucleic acid sequence flanked by appropriate flanking insertion region sequences without recombinant DNA molecule sequences. Recombinant viral progeny is thereafter produced in cell culture and can be selected for example genotypically or phenotypically, e.g. by hybridization, detecting enzyme activity encoded by a gene co-integrated along with the heterologous nucleic acid sequence or detecting the antigenic heterologous polypeptide expressed by the recombinant HVT immunologically. The selected recombinant HVT can be cultured on a large scale in cell culture whereafter recombinant HVT containing material or heterologous polypeptides expressed by said HVT can be collected therefrom.

According to the present invention a live recombinant HVT expressing one or more different heterologous polypeptides of specific pathogens can be used to vaccinate animals, particularly avian species such as chickens, turkeys, quails, pigeons and guinea fowl susceptible to these pathogens. Vaccination with such a live vector vaccine is preferably followed by replication of the recombinant HVT within the inoculated host, expressing in vivo the heterologous polypeptide along with the HVT polypeptides. The heterologous immunogenic polypeptides will then elicit an immunological response to said polypeptides as well as to HVT itself. If the heterologous polypeptide derived from a specific pathogen can stimulate a protective immune response, then the animal inoculated with a recombinant HVT according to the invention will be immune to subsequent infection by that pathogen as well as to infection by MDV. Thus, a heterologous nucleic acid sequence incorporated into the insertion region of the HVT genome according to the invention may be continuously expressed in vivo, providing a solid, safe and long lasting immunity to a pathogen.

A recombinant HVT according to the invention containing and expressing one or more different heterologous polypeptides can serve as a monovalent or multivalent vaccine.

A recombinant HVT according to the invention can also be used to prepare an inactivated vaccine.

For administration to animals, the recombinant HVT according to the presentation can be given inter alia by aerosol, drinking water, orally, in ovo inoculation, intradermally, subcutaneously or intramuscularly.

It is a further object of the present invention to produce subunit vaccines, pharmaceutical and diagnostic preparations comprising a heterologous polypeptide expressed by a recombinant HVT according to the invention. This can be achieved by culturing cells infected with said recombinant HVT under conditions that promote expression of the heterologous polypeptide. The heterologous polypeptide may then be purified with conventional techniques to a certain extent depending on its intended use and processed further into a preparation with immunizing, therapeutic or diagnostic activity.

The above described active immunization against specific pathogens will be applied as a protective treatment in healthy animals. It goes without saying that animals already infected with a specific pathogen can be treated with antiserum comprising antibodies evoked by a recombinant HVT according to the invention comprising a heterologous gene derived from the specific pathogen encoding an antigenic polypeptide. Antiserum directed against a recombinant HVT according to the invention can be prepared by immunizing animals, for example poultry, with an effective amount of said recombinant HVT in order to elicit an appropriate immune response. Thereafter the animals are bled and antiserum can be prepared.

EXAMPLE 1

1. Isolation of subfragments from the Us region of the HVT oenome

Chicken embryo fibroblasts (CEF) were infected with virus from HVT vaccine strain PB-THVI (commercially available from Intervet International, Holland) and incubated for 48 hours in roller bottles until the cultures reached 90% cytopathic effect (CPE). Cells were harvested, washed with phosphate buffered saline (PBS), centrifuged and resuspended in 20 mM Tris-HCl, pH 7.5, 10 mM EDTA at a density of 1 to $5 \times 10^8$ cells per ml. SDS was added to 0.5% final concentration and proteinase K (Boehringer) to 200 µg/ml. After 2 hours incubation at 37° C., an additional 100 µg/ml of proteinase K was added and incubation was continued for 1 hour. The solution was extracted twice with a mixture of phenol/chloroform (1:1) and nucleic acids were precipitated with ethanol. Total DNA from infected cells was dissolved in TE (10 mM Tris-HCl, pH 7.5, 1 mM EDTA) at a concentration of 0.5 mg/ml. Ten microgram of the DNA was incubated with 0.5 unit of Sau3A (Promega) for 10' at 37° C. in a 100 µl reaction volume according to the conditions recommended by the enzyme supplier. Reaction products were seperated on a 0.8% agarose gel and the size fraction between 16 and 20 kb was isolated. Hundred nanograms of these DNA fragments were ligated overnight at +4° C. with 1 µg of BamHI/EcoRI digested λEMBL3 DNA (Promega) in 10 µl of 30 mM Tris-HCl, pH 7.5, 10 mM MgCl$_2$, 10 mM DTT, 0.1 mM ATP, adding 1 U of T$_4$ DNA ligase (Boehringer). After ligation, one tenth of the reaction mixture was digested with BamHI in a 10 µl volume and DNA was packaged in vitro using commercial extracts (Promega) Recombinant phage was plated on appropriate E. coli host strain such as LE392 or K802 at a density of about 100 pfu/plate. Replicas of the dishes were prepared in duplicate using nitrocellulose filters according to Benton & Davis (1978). The first set was hybridized (Maniatis et al., 1982) with $^{32}$P-labelled DNA from uninfected CEF and the second with $^{32}$P-labelled DNA from HVT infected cells. After washing and exposure to X-ray film, images of the duplicate filters were superimposed in the correct orientation and several of the plaques giving a signal specifically with the probe made from infected cells were isolated and phage from it was amplified. One of these candidates, designated λHVT04, was analyzed in detail by restriction mapping of the 17.5 kb insert (FIG. 1). The sequence present in this fragment corresponded essentially to the Us region of the HVT genome, including flanking parts of the repeat structures (Igarashi, et al., 1987).

2. Insertion of βgalactosidase gene into the HVT genome using subfragments of the Us region Two of the XhoI fragments present in the insert of λHVT04 contained a unique BglII restriction site at the proper position in order to allow the in vivo recombination event with intact viral genomic DNA to take place. These two fragments were subcloned from λHVT04 by XhoI digestion and ligation with the plasmid vector pGEM3Z (Promega) digested with SalI. The resulting plasmid constructs pMD07 and pMD12, carrying the XhoI fragments as indicated in FIG. 1, were linearized by means of the unique BglII restriction site and ligated with a 4.0 kb expression cassette flanked by BamHI sites and containing the B-galactosidase gene from E. coli controlled by the early promotor from SV40. This expression cassette has been derived from pCHI10, a plasmid commercially available from Pharmacia, by replacing a 72 bp SphI fragment near the SV40 origin of replication as present in pCH110 by a double stranded synthetic oligonucleotide with the following structure:
5'-GGATCCGTCGACCATG-3'(SEQ. I.D.No:6)
3'-GTACCCTAGGCAGCTG-5'(SEQ. I.D. No. 15)

Figure 2A:
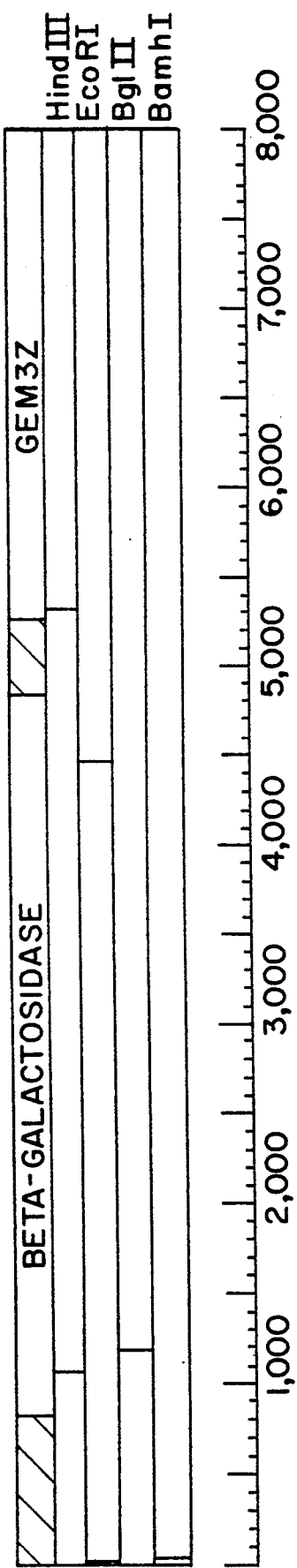
FIG. 2 A is a restriction map of pMD07gal.
Figure 2B:
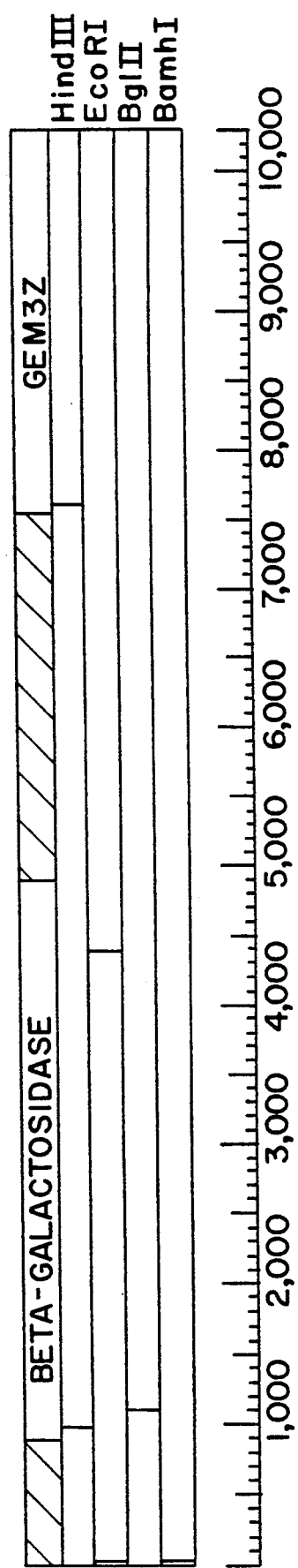

Insertion of the linker between the two SphI restriction sites of pCHI10 does not restore the recognition sequence for SphI on either site and creates both a BamHI and SalI site upstream of the SV40 early promotor. Subsequent digestion of this construct with BamHI generates a 4.0 kb expression cassette used above for insertion in the BglII site from pMD07 and pMD12, thereby resulting in the plasmids pMD07gal and pMD12gal for which the restriction maps are shown in FIG. 2. Linearized DNA of the plasmids pMD07gal and pMD12gal was introduced together with total DNA prepared from HVT infected cells into CEF by a method based on the calcium phosphate DNA precipitation according to Graham and v.d. Eb (1973). Two micrograms of plasmid DNA from the constructs containing the β-galactosidase gene flanked by HVT homologous sequences were mixed with 15 µg of DNA from HVT infected cells in a final volume of 560 µl H$_2$O and added to 750 µl of HBSP (20 mM KCl, 560 mM NaCl, 24 mM glucose, 3 mM Na2HP04, 100 mM HEPES, pH 7.0). Precipitates were formed by gradually adding 190 µl of 1M CaCl$_2$ solution and incubating the mixtures at room temperature for 30 minutes. In the meantime, 15 ml of a suspension of secondary CEF from 10 day old embryos in medium 6/B8, for which the composition is based on Glasgow's modification of Eagle's Minimal Essential Medium supplemented with 2% of fetal calf serum, were seeded in $\phi$ 10 cm dishes at a density of $5 \times 10^5$ cells per ml. Calcium phosphate precipitated DNA was gently added to the cell suspension and dishes were incubated at 37° C. in a humidified incubator containing 5% CO$_2$ in air. After 5 hours, medium was removed and 10 ml of a solution containing equal volumes of HBSP and 30% glycerol was layered onto the cells. After a one to two minute incubation, the solution was removed, cells were washed with medium 6/B8 and dishes were incubated with fresh medium for 3 to 5 days until viral CPE developed. Plaques that contained recombinant HVT virus expressing β-galactosidase activity were identified by their capacity to convert the substrate Bluogal (Gibco-BRL), a chemical derivative of 5-bromo-4-chloro-3-indolyl-β-D-galactoside, into a blue reaction product. Plates were stained with 0.2 mg/ml of Bluogal freshly dissolved in dimethylsulfoxide and incubated until blue plaques were detected. Transfection with the β-galactosidase derivatives from pMD07 and pMD12, all resulted in a significant (>5) percentage of blue plaques. Positive plaques from the transfection series with pMD07 and pMD12 were picked macroscopically and mixed with fresh CEF in order to amplify the virus. Cells were harvested when CPE was visible and lysates were prepared in Calstab buffer (74.35 g sucrose, 0.52 g KH$_2$PO$_4$, 2.58 g Na$_2$HPO$_4$.2H$_2$O and 0.92 g sodium glutaminate per liter of H₂O) including 1% of bovine serum albumin, by sonifying plastic tubes containing the extract in a Vibracell 300 cup horn device for 3 minutes at 15° C. Cell free virus was plated on fresh CEF for titration and plaques containing blue-staining recombinant HVT virus were detected and amplified as described above. This cycle was repeated until more than 95% of the viral plaques scored positive when staining the cultures with Bluogal. In particular four clones, designated as A4-1/A10-4 both derived from pMD07 and E1/E2 derived from pMD12, were selected for the preparation of virus stocks which served the vaccination experiments in chickens. In addition, part of the stock was used for the preparation of total DNA from infected CEF. DNA digested with XhoI was run on agarose gels and transferred to nitrocellulose sheets according to Maniatis et al. (1982). Hybridizations of the samples from A4-1/A10-4 and E1/E2 in comparison to XhoI digested DNA of the non-recombinant HVT virus, using the non-disrubted XhoI fragments as probes, indicated the expected increase in size of the original fragments in pMD07 and pMD12 due to the insertion of the $\beta$-galactosidase cassette.

Figure 3A:
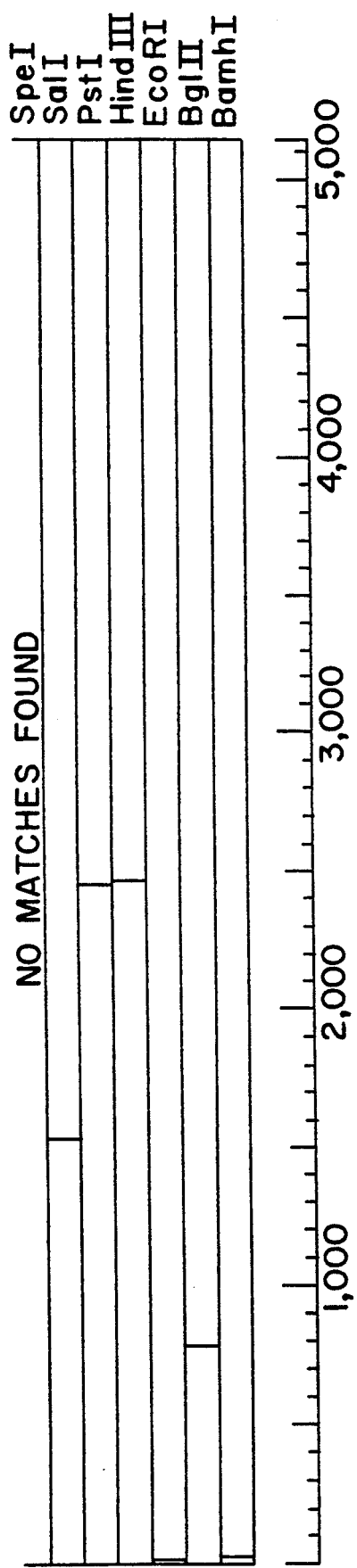
FIG. 3 A is a restriction map of pMD12.

The $\beta$-galactosidase marker gene was used to show that also ORF-4 and ORF-5 represented a potential insertion region. For this purpose, the 1117 bp SpeI fragment in pMD12 between nucleotide position 2311 in ORF-4 and 3428 in ORF-5, was replaced by a synthetic 16 base double stranded oligomer creating a new and unique Sal I site in pMD12 thereby deleting a significant part of both ORF-4 and ORF-5. The restriction map of this plasmid, designated pMD40, is presented in FIG. 3A. The $\beta$-galactosidase marker gene used for insertion was derived from pCH110 (Pharmacia) by first exchanging the unique Bam HI site with Sal I and subsequently replacing the 72-bp SphI fragment by a double stranded synthetic linker containing both a Bam HI and Sal I restriction site as described above.

Figure 3B:
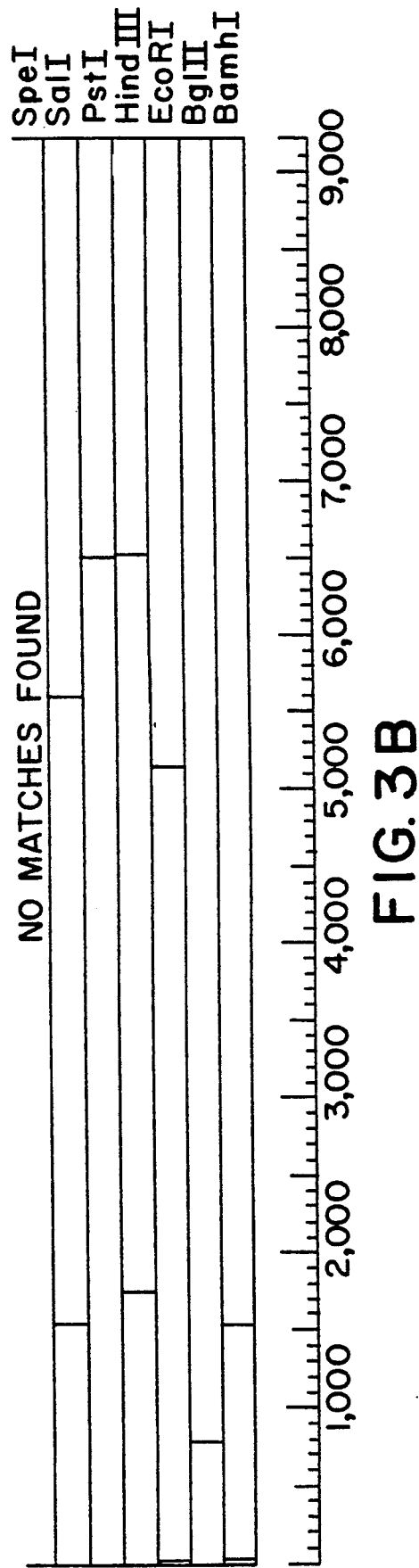

The $\beta$-galactosidase marker gene is now located on a 4.0 kb DNA fragment flanked by Sal I sites and can be transferred as such to the newly created Sal I site in pMD40, thereby resulting in plasmid pMD44 (see FIG. 3B).

Linearized DNA of pMD44 is co-transfected with DNA from HVT infected cells into secundary CEF as described above. Plates are incubated until CPE has developed. Staining of the culture dishes with Bluogal identified a significant percentage of HVT plaques expressing $\beta$-galactosidase activity.

These results were comparable with initial observations made after insertion of the marker gene in ORF-2 and ORF-3.

EXAMPLE 2

Vaccination of chickens with recombinant HVT expressing $\beta$-galactosidase activity White leghorn day-old chickens were inoculated i.m. with either 50 or 1000 pfu of the virus stocks A4-1 and E1. An equal dose of the parental HVT vaccine strain PB-THVI was given to the control animals. At day 8 and 15, blood samples were collected and white blood cells were separated on Ficoll/Hypaque gradients. White blood cells were inoculated onto secondary CEF and the number of plaques was determined relative to the number of cells inoculated. The results of these titrations are shown in Table 1 and demonstrate that recombinant HVT virus, containing a $\beta$galactosidase gene inserted in either of the unique BglII restriction sites within each of the XhoI subfragments present in pMD07 and pMD12 respectively, was able to induce vireemias in chickens at comparable times and levels relatively to the non-recombinant PB-THVI vaccine strain. Staining with Bluogal of some of the white blood cell titrations on CEF showed that >90% of the virus recovered from the infected birds still expressed the $\beta$-galactosidase gene. In addition, significant ELISA antibody titres to $\beta$-galactosidase were demonstrated in the serum samples of individual animals 35 days after inoculation. Therefore, it was concluded that a particular region of the Us from the HVT genome, as defined by the contiguous sequence present in pMD07 and pMD12, can be used for the stable integration of foreign genes without affecting essential functions of the HVT virus such as those necessary for infection and replication. In addition, it could be shown that a foreign gene inserted in this region does express a functional protein which can induce high levels of antibody titres in the serum of infected animals.

TABLE 1

| | | Vireemia of white blood cells (WBC) induced by recombinant HVT | | | |
|---|---|---|---|---|---|
| | | 8 days p.v. | | 15 days p.v. | |
| Virus | Dose (pfu) | calculated plaques | Nos. cells inoculated ($\times 10^5$) | calculated plaques | Nos. cells inoculated ($\times 10^5$) |
| A4-1 | 50 | 8* | 6.8 | 21 | 14.7 |
| | | 1* | 1.5 | 44 | 35.5 |
| | | 20 | 3.2 | 17 | 27.5 |
| A4-1 | 1000 | 30 | 5.7 | 7 | 28.2 |
| | | 8* | 1.5 | 20 | 16.5 |
| | | 13 | 1.2 | 18 | 30.7 |
| | | 7* | 1.7 | | |
| E-1 | 50 | 95 | 0.7 | 14 | 10.7 |
| | | 1600 | 3.3 | 150 | 17.2 |
| | | 170 | 2.5 | 55 | 9.0 |
| | | 2* | 1.8 | 85 | 13.7 |
| | | 1* | 2.1 | 30 | 13.5 |
| E-1 | 1000 | 2* | 1.8 | 24 | 19.2 |
| | | 1* | 1.3 | 75 | 30.5 |
| | | 15 | 5.2 | 15 | 25.0 |
| PB1 | 50 | 13 | 1.7 | 110 | 14.5 |
| | | 26 | 1.5 | 130 | 34.2 |
| | | 27 | 3.0 | 110 | 14.5 |
| | | 12 | 3.7 | 290 | 20.2 |
| | | 6* | 2.0 | 36 | 8.2 |
| PB1 | 1000 | 110 | 6.5 | 32 | 15.5 |
| | | 185 | 4.0 | 600 | 122.5 |
| | | 1150 | 4.7 | 280 | 19.5 |
| | | 65 | 3.0 | 345 | 6.7 |
| | | 330 | 3.0 | 175 | 27.5 |

*read 5 days after inoculation of WBC on CEF plates
other read after 3 days post inoculation

EXAMPLE 3

Sequence analysis of part of the Us region of HVT.

The inserts of plasmids pMD07 and pMD12, corresponding to the respective XhoI restriction fragments from the HVT genome as shown in FIG. 1, were submitted to detailed nucleotide sequence analysis using double stranded DNA preparations in dideoxy chain termination reactions according to Sanger et al. (1977). Priming of the reaction was done from within the SP6 and T7 promotor sites in the pGEM3Z plasmid vector flanking the respective HVT genomic fragments. The analysis was completed by introducing progressive deletions entering the respective fragments in one orientation only. These progressive deletions were introduced using the enzyme Exonuclease III, a single strand exonuclease only recognizing double stranded DNA and hydrolizing one strand of the duplex in the 3' to 5' orientation. Selecting a restriction site that creates a 5'-overhanging or blunt-ended extremity near the end of the fragment to be analyzed, in combination with a second restriction enzyme generating a 3' single stranded extremity which protects the primer initiation site SP6 or T7 in the plasmid vector from being degraded by the Exonuclease III, forces the enzyme to remove one strand of the inserted DNA fragment such as present in pMD07 or pMD12. Samples were taken from the reaction mixture at 30 seconds interval and treated according to the procedures described by Henikoff (1984), generating recirculized DNA molecules which are transformed into an appropriate E. coli host strain. Plasmid DNA minipreparations of individual colonies were analyzed by restriction mapping for the size of the deletion introduced into the original 1.2 and 3.5 kb fragments of pMD07 and pMD12 respectively. A series of candidates containing progressive deletions entering the fragment in one orientation, were analyzed by nucleotide sequencing using the double stranded DNA from mini-preparations in the chain termination reaction. Reaction products were separated on denaturing acrylamide gels and visualized on X-ray film by autoradiography. Banding patterns were read with a digitizer and data were assembled and analyzed using the shot-gun handler and other software from a Gene-Master workstation (Bio-Rad).

The XhoI restriction fragment adjacent the XhoI fragment present in pMD12 was subcloned from λHVT04 (FIG. 1 into pMD36 and partially sequenced according to the same procedure described above.

EXAMPLE 4

After the identification and detailed analysis of a region within the HVT genome were gene insertions are allowed to be made, a recombinant: HVT virus can be constructed with any gene other then the one encoding β-galactosidase. However, particularly those genes are of interest which encode relevant antigens from both related and non related avian pathogens. An example of such an application will be described in the following paragraphs. The gene of interest encodes the 157 kd precursor molecule for the peplomer protein of Infectious Bronchitis Virus (IBV), a highly contagious coronavirus of chickens. This glycosylated protein is a major component of the typical surface structures, also known as spikes, present on all coronaviruses including IBV. A cDNA copy of this gene was isolated from IBV strain M41, a strain belonging to the Massachusetts serotype, and placed behind a promotor element derived from the long terminal repeat sequence (LTR) of Rous Sarcoma Virus (RSV). The gene including the promotor was then transferred to the unique BglII restriction site in pMD07, the same as used previously for the insertion of the β-galactosidase expression cassette, and recombined into the viral genome of HVT. Recombinant progeny of the virus was screened for the expression of the spike gene and positive candidates were isolated and cloned by one or more platings at limiting dilution. Homogenous stocks of the recombinant IB/HVT virus were established and used for subsequent in vivo and in vitro characterization.

1. Isolation of the soike qene from IBV strain M41

Virus from IBV strain M41 was grown in 10 day old embryonated eggs, by inoculating the allantoic cavity with $10^4$ median egg infectious dose per egg. After 24 hours incubation at 37° C., eggs were chilled overnight at 4° C. Allantoic fluid was harvested taking care to keep it cool on ice. Red blood cells and debris were removed by centrifugation at 4° C. and 6000×g for 30'. Virus was pelleted from the supernatant at 54,000 x g in a Beckmann Type 19 rotor for 4 hours at 4° C. The pellet was resuspended in cold TNE (10 mM Tris-HCl, 100 mM NaCl, 1 mM EDTA, pH 7.5) by repeated passage through a syringe needle and layered onto a 32 ml linear gradient of 20–60% sucrose in TNE. After overnight centrifugation at 4° C. in a SW28 rotor at 24,000 rpm, virus band was collected through the side wall puncturing the tube with a syringe. After dilution with 2 volumes TNE, virus was pelleted in a SW28 rotor at 18,000 rpm for 90' at 4° C. Material was resuspended in a small volume of TNE and sodium dodecyl sulphate was added to a final concentration of 0.5%. Preparation was digested with proteinase K (Boehringer) at 200 μg/ml for 2 hours at 37° C. and extracted twice with a 1:1 mixture of phenol/chloroform. Viral RNA in the aqueous phase was precipitated with 2 volumes of ethanol in the presence of 0.1 M sodium acetate pH 6.0 at −20° C. After centrifugation and rinsing the tube with ethanol, the pellet was dried under vacuum and dissolved in sterile water to give a RNA concentration of 0.5 mg/ml. Preparation contained >90% of IBV genomic RNA as checked by agarose gel electrophoresis and was stored at −20° C. First strand cDNA synthesis was primed with oligo $(dT)_{12-18}$ in the presence of AMV reverse transcriptase using 5 μg of viral RNA in a 75 μl reaction volume. After incubating 30' at 44° C., DNA/RNA hybrids were denatured by heating 30' at 100° C. followed by synthesis of the second strand in the presence of the large fragment from E. coli DNA polymerase I incubating the reaction for 2 hours at 20° C. cDNA was precipitated with ethanol and digested with 10 units of $S_1$ nuclease in a 200 μl reaction volume for 30' at 37° C. Reaction products were layered onto 3.2 ml of a 5-20% sucrose gradient in 10 mM Tris-HCl, 5 mM EDTA, 500 mM NaCl, pH 7.5 and centrifuged in a SW65 rotor at 30,000 rpm for 16 hours at 15° C. Material sedimenting with a size between 500 and 5000 base pairs, was collected, ethanol precipitated and dissolved in 20 μl of 0.1 SSC (15 mM NaCl, 1.5 mM sodium citrate).Ends of the double stranded cDNA were extended with 10 to 15 dG residues by a 2' incubation at 37° C. with 15 units terminal transferase (Gibco-BRL) in a 30 μl reaction volume according to the conditions recommended by the enzyme supplier. Reaction was stopped with 5 mM EDTA. Ten nanograms of tailed cDNA were heated for 2' at 65° C. with a 25-molar excess of the phosphorylated synthetic oligomer 5'-dAATTCCCCCCCCCCCC-3' (CSEQ. ID No: 7)in a final volume of 10 μl TEN and annealed together by overnight incubation at 50° C. Ligation with 10 μg of EcoRI digested λgt10 DNA (Huynh et al., 1985) was in 20 μl of 30 mM Tris-HCl, pH 7.5, 10 mM MgCl₂, 10 mM DTT, 0.1 mM ATP, adding 1 unit of T4 DNA ligase and incubating overnight at 4° C. DNA was added to in vitro packaging reaction mixture (Promega) and a cDNA library from IBV strain M41 was established by selecting for recombinant phages after plating on an hflA strain of E. coli.

The library was screened for cDNA clones encoding fragments of the spike protein by plating one to two hundred pfu in a petri dish on a lawn of E. coli. Duplicate filters of nitrocellulose were prepared (Benton and Davis, 1978) and incubated overnight at 42° C. with 32P-labelled synthetic oligomers in a hybridization solution containing 10 mM Tris-HCl, pH 7.5, 1 M NaCl, 0.1% SDS and 4×Denhardt's solution (Maniatis et al., 1982).

The three synthetic oligomers used as probes in these hybridizations contained the following nucleotide sequence structure:

I.       5'-dTTAGGTGGTCTGAAGGCACTTTG-GTAGTAGTA-3'(SEQ. ID NO: 8)

II.     5'-dTACCTACTAATTTACCACCAGAAAC-TACAAACTGCTG-3'(SEQ. ID NO:9)

III.    5'-dTGGATCATTAAACAGACTTTT-TAGGTCTGTATTGTT-3'(SEQ. ID NO:10)

Recombinant phages giving a signal with one or preferentially two of these probes were selected and plaque purified by standard procedures (Maniatis et al., 1982). cDNA fragments from λ phage recombinants were flanked by EcoRI restriction sites and transferred as such into the EcoRI site from plasmid cloning vector pGEM3Z (Promega). Restriction analysis and partial sequencing on two candidates showed that one encoded the complete $S_1$ and the other encoded the $S_2$ moiety of the spike gene. The sequence of these two DNA fragments partially overlapped with each other in particular with respect to the unique MluI-restriction site near the $S_1/S_2$ junction. This site was then used to assemble the two fragments mentioned above and resulted in a plasmid construction with a 3,7 kb BamHI insert, carrying the complete gene encoding the precursor for the protein peplomer from IBV strain M41.

Figure 4:
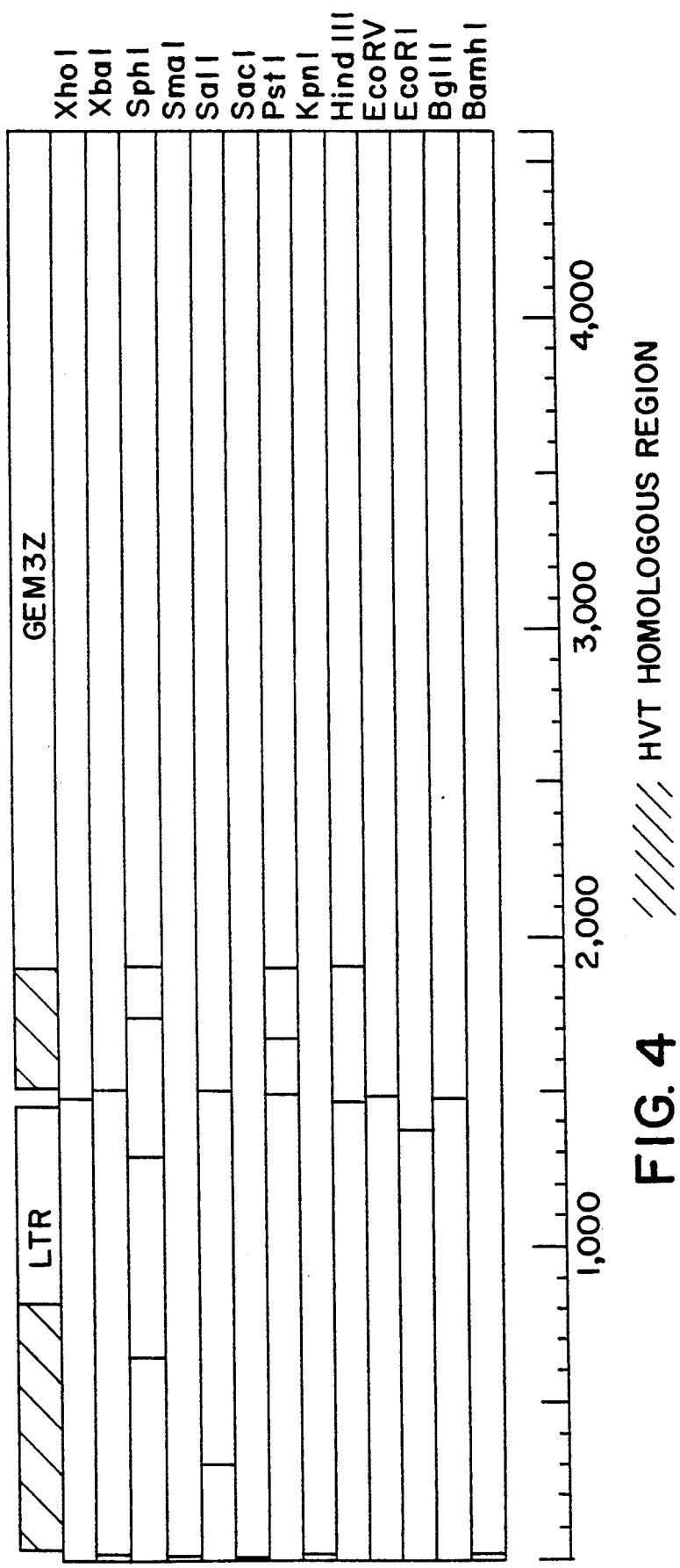
FIG. 4 is a restriction enzyme map of pVECO4 with the LTR promotor inserted.
Figure 5:
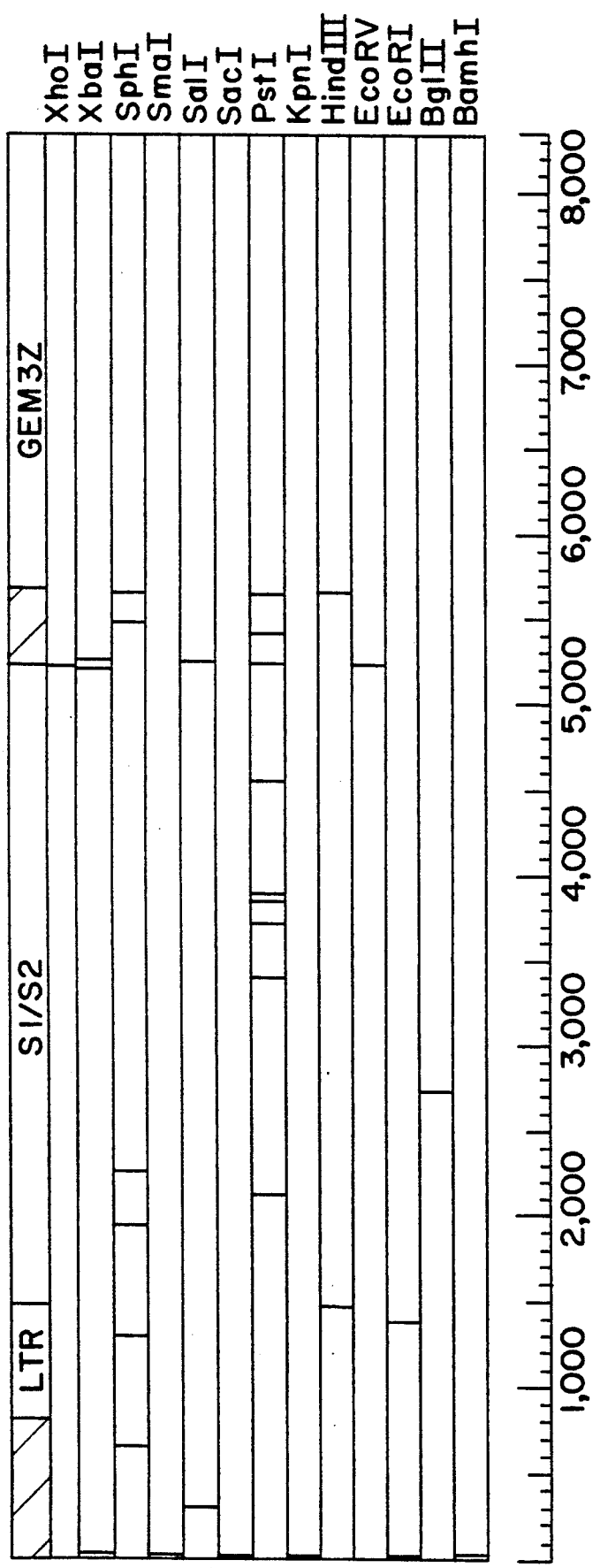
FIG. 5 is a restriction enzyme map of pIB18 showing the 3.7 kb BamHI fragment carrying the spike gene from IBV strain M41 inserted into the BglII site of pVECO4 downstream of the LTR promotor.

2. Construction of the HVT recombination plasmid pIB18 encoding the spike gene from M41 controlled by a LTR promotor A strong promotor which could direct the expression of foreign genes after their insertion into the genome of the HVT virus was selected from the LTR sequence of RSV. The promotor has been mapped on a 580 bp NdeI/HindIII restriction fragment from pRSVcat (Gorman et al., 1982) and was inserted between the HindIII and PstI sites of pGEM3Z (Promega) by means of double stranded synthetic linkers on both sides of the fragment. The connection between the HindIII site from the vector pGEM3Z and the NdeI site of the RSV fragment carrying the LTR promotor was made with a 30 bp linker containing cohesive ends compatible with HindIII on one and NdeI on the other site. However, after ligation both restriction sites are not restored due to deliberate modifications in the outer nucleotides of the six base pair recognition sequence. In addition to the removal of these two sites, a new restriction site (BamHI) present within the linker itself was created at the corresponding position. A second 20 bp linker was synthesized which connected the HindIII site from the LTR fragment to the PstI site from pGEM3Z, in this case without destruction of the recognition sequence on either of the ends and adding the three convenient unique restriction sites BglII, XhoI and EcoRV to those already present in the polylinker of pGEM3Z, e.g. PstI, SalI, XhoI and BamHI. The resulting derivative of pGEM3Z, designated pVEC01, therefore contains a 650 bp restriction fragment carrying the LTR promotor sequence immediately followed by seven restriction sites available for the insertion of foreign genes. The 650 bp fragment is flanked on either end by a BamHI restriction site and has been transferred as such to the unique BglII site present in the 1.2 kb HVT insert from pMD07. The cohesive ends generated by these two restriction enzymes are compatible but ligation does not restore either of the original recognition sequences for BglII or BamHI. One of the resulting constructs, carrying the LTR in the orientation towards the $TR_s$, was designated pVEC04 and checked by restriction mapping (FIG. 4). The structure of this universal HVT recombination vector allows the insertion of foreign genes immediately downstream of the LTR promotor and subsequent integration of the complete expression cassette into the HVT genome by in vivo recombination. The positions of the different restriction sites downstream of the LTR in particular those for the enzymes BglII, XhoI and EcoRV are designed in such a way that even multiple gene insertion can be envisaged. A first application for this vector has been the construction of a recombinant HVT virus expressing the spike gene from IBV strain M41, the isolation of which has been described in the previous paragraph. A 3.7 kb BamHI restriction fragment carrying the spike gene from M41, was inserted into the unique BglII site of pVEC04 downstream of the LTR promotor. Again this manipulation does not restore either of the restriction sites after ligation. One of the candidates having the gene inserted in the correct orientation relative to the LTR promotor was analyzed by restriction mapping confirming the expected structure as presented in FIG. 5. This plasmid was designated pIB18 and used subsequently in the co-transfection of chicken embryo fibroblasts (CEF).

3. Genomic insertion of the spike gene from IBV into HVT and expression of the peplomer protein Linearized DNA from pIB18 was transfected together with total DNA from HVT infected chicken cells according to the method described in example I for the construction of β-galactosidase recombinants.

Detection of HVT recombinants expressing the spike protein was done by immunofluorescence staining using mono- or polyvalent sera against IBV. Primary cultures after the transfection were passed once on fresh CEF, harvested and sonicated as described before in example 1. After titration of the cell free lysates, microtitre plates with CEF were infected at limiting dilution using less then one pfu per well and incubated until CPE was detected. Cell suspensions from each of the wells separately were split over duplicate microtitre plates together with fresh CEF and reincubated for two days. One of the plates was then fixed, stained with IBV specific sera and inspected for immuno fluorescence under the microscope scoring those wells which contained a majority of IBV-positive staining HVT plaques.

Viable infected cells were recovered from the corresponding wells of the duplicated microtitre plate and amplified by one or two passages on fresh CEF. This cloning procedure based on limiting dilution was repeated a number of times and resulted in several independent isolates of the recombinant HVT virus which all stained positively in the IBV specific immunofluorescence assay on infected cell cultures.

EXAMPLE 5

1. Isolation of genes encoding the fusion (F) and hemagglutinin (HN) protein from Newcastle Disease Virus (NDV)

Virus from the NDV vaccine strain Clone 30 (Intervet International, Holland) was grown on embryonated eggs for 30 hours and allantoic fluid harvested after overnight incubation at +4° C. Virus was purified over a single sucrose gradient and genomic RNA was extracted by proteinase k digestion in the presence of SDS.

First strand cDNA synthesis was performed with reverse transcriptase using a random 10 base oligomer at 20 μg/ml to prime the reaction. Second strand synthesis, S1-treatment and following steps including insertion into the λgt10 vector were done as described previously under section 1 of example 4. Screening of the library for F-gene specific sequences was done by plaque hybridization with the 32P-labelled oligonucleotides.

I      5'GGCAGGCCTCTTGCGGCTGCAGG-GATTGTGGTAACAGG 3'(SEQ. ID NO: 11)
II     5'GCAAAAGGC-GCAACAGAAGACCTTGTTGTGGCTTGGC 3'(SEQ. ID NO: 12)

recognizing 5' and 3' extremities of the coding region, respectively. Identification of HN-gene sequences was done with the oligonucleotides.

III    5'GAAAGAGAGG-CGAAGAATACATGGCGCTTGGTATTCCGG 3'(SEQ. ID NO. 13)
IV     5'GAAATATCTAATACTCTCTTCGG-GGAATTCAGGATCGT 3'(SEQ. ID NO: 14)

The sequence of these probes was designed by comparing published data on NDV-strains Australia-Victoria (McGinnes et al., 1986), Italien (Espion, et al., 1987 and Wemers, et al., 1987), Beaudette (Chambers et al., 1986 and Millar et al., 1986) and D26 (Sato et al., 1987).

Positive candidates giving a signal with at least two of the probes were isolated and characterized by restriction mapping. From this series, two were selected covering respectively the F and HN from NDV strain Clone 30.

The DNA inserts were transferred to the plasmid vector pGEM4Z and manipulated with the exonuclease Bal 31 to remove excessive or overlapping sequences up- or downstream of the actual coding region of the F- and HN-gene.

This resulted in the plasmids pNDV01 and pNDV03 containing the complete gene coding for F respectively HN flanked by Bam HI restriction sites.

2. Genomic insertion of F- and HN-gene from NDV into HVT

Bam HI fragment of plasmid pNDV01 and pNDV03, containing the genes encoding F and HN respectively, were inserted into the Bgl II site of the HVT recombination vector pVEC04 resulting in pNDV04 and pNDV05.

Figure 6A:
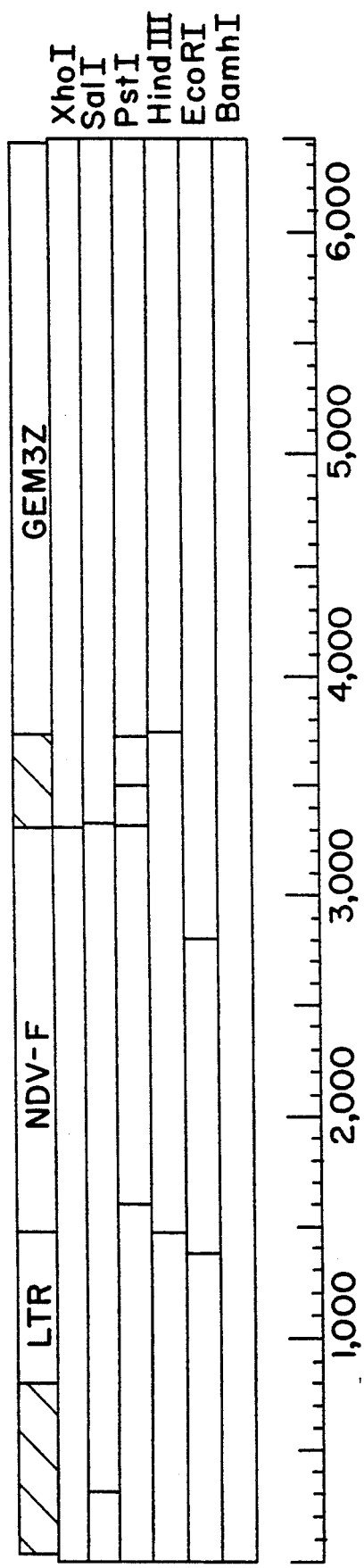
FIG. 6 A is a restriction map of pNDVO4.
Figure 6B:
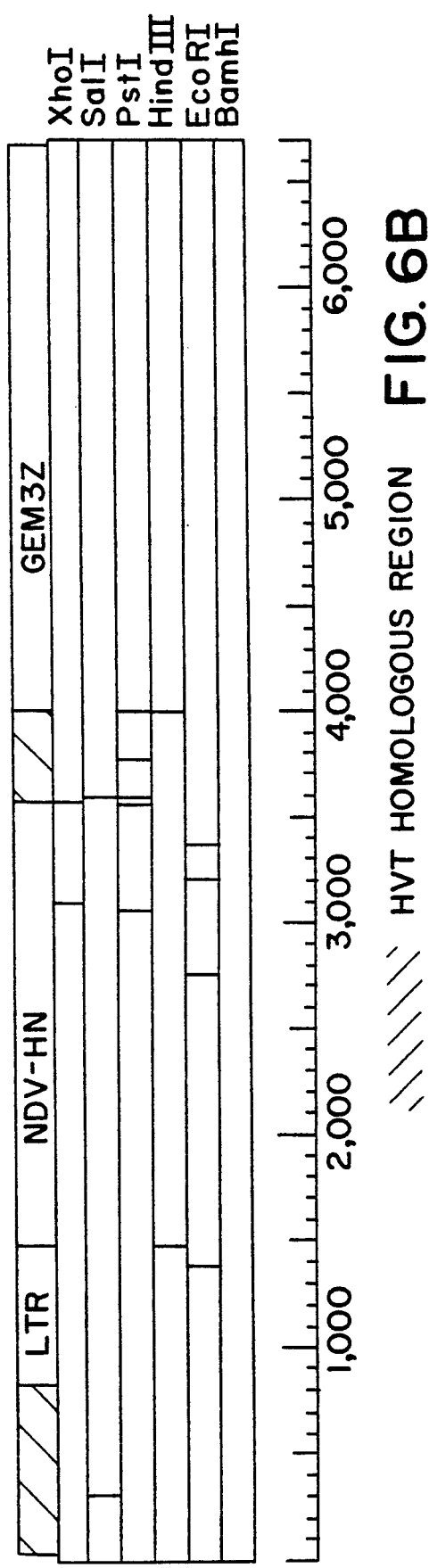

Correct orientation of inserted genes relative to the LTR promotor was verified by restriction analysis based on the physical map of these construct shown in FIG. 6.

DNA from these plasmids is co-transfected together with DNA from HVT infected cells into CEF as described in section 2 of example 1.

After amplification of transfected cultures, cell free lysates were established and plated onto microtiter dishes.

Detection of HVT recombinants expressing the F or HN protein was done by immunofluorescense staining using polyvalent NDV sera or monoclonal antibodies against specific NDV antigens.

Enrichment of HVT recombinant virus was done by limiting dilution as described in section 3 of example 4. Establishment of a homogenous recombinant virus preparation was done by single plaque isolation and testing for expression of F respectively HN in infected CEF by immunofluorescence staining.

LEGENDS TO THE FIGURES

FIG. 1

Restriction enzyme map of a DNA fragment essentially corresponding to the Us region of the HVT genome. The relative position of the insertion,-region consisting of four open reading frames and non-coding sequences in between is indicated.

FIG. 2

A) Restriction map of pMD07gal. This plasmid has been derived from pMD07 by inserting the B-galactosidase gene into the unique BglII restriction site present in the 1.2 kb XhoI fragment of the HVT genome.

B) Restriction map of pMD12gal. This plasmid has been derived from pMD12 by inserting the B-galactosidase gene into the unique BglII restriction site present in the 3.5 kb XhoI fragment of the HVT genome.

FIG. 3

A) Restriction map of pMD40. A 1117 bp SpeI fragment present in pMD12 was replaced by a synthetic oligonucleotide containing a SalI site.

B) Restriction map of pMD44. Derived from pMD40 by insertion of a 4.0 ks B-galactosidase marker gene flanked by SalI sites into the SalI site of pMD40.

FIG. 4

Restriction enzyme map of pVEC04 showing the LTR-promotor inserted into the unique BglII site of the 1.2 kb XhoI HVT fragment from pMD07.

FIG. 5

Restriction enzyme map of pIB18 showing the 3.7 kb BamHI fragment carrying the spike gene from IBV strain M41 inserted into the BglII site of pVEC04 downstream of the LTR promotor.

FIG. 6

A) Restriction map of pNDV04. Plasmid contains NDV-F gene flanked by BamHI sites inserted into Bgl II site of pVECO4 (see FIG. 4).

B) Restriction map of pNDV05. Plasmid contains NDV-HN gene flanked by BamHI sites inserted into Bgl II site of pVECO4 (see FIG. 4).

References

1. Benton, W.D. and Davis, R.W. (1978), Science, 196, 180.
2. Chambers et al. (1986), J. Gen. 67, 2685.
3. Espion et al. (1987), Arch. Virol. 95, 79.
4. Gorman, C. et al. (1982), Proc. Natl. Acad. Sci. USA, 79.6777.
5. Graham, F. and v.d. Eb, A. (1973), Virology, 52, 456.
6. Henikoff, S. (1984), Gene, 28.35.
7. Huynh, T.V., et al. (1985) in "DNA cloning, Vol. I", ed. D. Glover, pag. 49.
8. Igarashi, T., et al. (1987), Virology, 157, 351.
9. Maniatis, T., et al. (1982) in "Molecular cloning", Cold Spring Harbor laboratory.

10. McGinnes et al. (1986), Virus Res. 5, 343.
11. Millar et al. (1986), J. Gen. Virol. 67. 1917.

12. Sanger, I., et al. (1977), Proc. Natl. Acad. Sci. USA, 74.5463.
13. Sato et al. (1987), Virus Res. 7, 241.
14. Wemers et al. (1987), Arch. Virol. 97, 101.

We claim:

1. A recombinat comprising a heterologous nucleic acid sequence, said nucleic acid sequence being introduced in an insertion region of the HVT genome which comprises the genomic region from the end of ORF-1 through ORF-5 located within a DNA fragment of the HVT genome having a restriction enzyme map defined by FIG. 1.

2. A recombinant HVT according to claim 1, wherein said nucelic acid sequence being introduced in an insertion region of the HVT-genome that corresponds with the DNA sequence between nucleotide positions 82 and 4504, defined by the DNA sequence shown in SEQ ID NO: 1.

3. A recombinant HVT according to claim 1, wherein the insertion region is selected from the open reading frames consisting of ORF-2, ORF-3, ORF-4 and ORF-5.

4. A recombinant HVT according to claim 3, wherein the heterologous nuceic acid sequence is incorporated at the BglII restriction site present in ORF-2 or ORF3.

5. A recombinant HVT according to claim 1, wherein at least a part of the HVT nucelic acid sequence with the insertion region is deleted.

6. A recombinant HVT according to claim 1, wherein the heterologous nucleic acid sequence encodes a polypeptide an is under control of a promoter regulating the expression of said nucleic acid sequence in a cell infected with said recombinant HVT.

7. A recombinant HVT according to claim 1, wherein the heterologous nucleic acid sequence encodes an antigen of an avian pathogen.

8. A recombinant HVT according to claim 7, wherein the antigen is selected from the group consisting of Marek's disease Virus, Infectious Bronchitis Virus, Newdastle Disease Virus and Infectious Bursal Disease Virus.

9. A nucleic acid sequence comprising a gene heterologous to HVT, or part thereof, controlled by a promoter, flanked by DNA sequences derived from the insertion region of the HVT genome which corresponds to the HVT genomic region from the end of ORF-1 through ORF-5.

10. A recombinant DNA molecule comprising a nucleic acid sequence according to claim 9.

11. A nucleic acid sequence according to claim 9 wherein said sequence transforms a host cell.

12. A process for the preparation of a recombinant HVT according to claim 1 comprising co-transfecting an appropriate cell culture with i. HVT DNA and ii.) a recombinant DNa molecule comprising a nucleic acid sequence comprising a gene heterologous to HVT or part thereof, controlled by a promoter flanked by DNA sequences derived from the insertion region of the HVT genome which corresponds to the HVT genomic region from the end of ORF-1 through ORF-5.

13. A culture comprising cells infected with a recombinant HVT according to claim 1.

14. A recombinant HVT according to claim 2, wherein the insertion region is selected from the open reading frames consisting of ORF-2, ORF-3, ORF-4 and ORF-5.

15. A recombinant HVT according to claim 14, wherein the heterologous nucleic acid sequence is incorporated at the BglII restriction site present in ORF-2 or ORF-3.

16. A recombinant HVT according to claim 5, wherein the heterologous nucleic acid sequence encodes a polypeptide and is under control of a promoter regulating the expression of said nucleic acid sequence in a cell infected with said recombinant HVT.

17. A recombinant HVT according to claim 5, wherein the heterologous nucleic acid sequence encodes an antigen of an avian pathogen.

18. A nucleic acid sequence according to claim 10, wherein said sequence transforms a host cell.

19. A culture comprising cells infected with a recombinant HVT according to claim 5.

* * * * *

UNITED STATES PATENT AND TRADEMARK OFFICE
CERTIFICATE OF CORRECTION

PATENT NO. : 5,187,087
DATED : February 16, 1993
INVENTOR(S) : Sondermeijer et al.

It is certified that error appears in the above-identified patent and that said Letters Patent is hereby corrected as shown below:

On the title page, item [75], delete "Pulus"
and replace with -- Paulus --.

On title page, after "Attorney, Agent or Firm"
Donna", delete "Bobwicz" and replace with -- Bobrowicz --.

In the Abstract, second and third lines, delete "heterolo-gus" and replace with -- heterologous --.

Col. 31, claim 1, line 1, delete "recombinat" and replace with --recombinant--

Col. 32, claim 8, line 3, after "Marek's", delete "disease" and replace with -- Disease --.

Col. 32, claim 8, line 4, delete "Newdastle" and replace with --Newcastle--.

Signed and Sealed this

Sixteenth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.  : 5,187,087
DATED       : February 16, 1993
INVENTOR(S) : Paulus Sondermeijer et al.

It is certified that error appears in the above-identified patent and that said Letters Patent is hereby corrected as shown below:

Please delete on the title page, in item [30], the "Foreign Application Priority Data" section, the number "89.2003071.9" and replace with -- 89.203071.9 --.

Signed and Sealed this

Twenty-sixth Day of April, 1994

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 15

( v i ) CURRENT APPLICATION DATA:
    ( A ) APPLICATION NUMBER: 07/621,193
    ( B ) FILING DATE: November 30, 1990

( 2 ) INFORMATION FOR SEQ ID NO:1:

( i ) SEQUENCE CHARACTERISTICS:
    ( A ) LENGTH: 4527 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Herpesvirus of turkey
    ( B ) STRAIN: PB-THV1

( i x ) FEATURE:
    ( A ) NAME/KEY: CDS
    ( B ) LOCATION: 1..81
    ( D ) OTHER INFORMATION: /label=endofORF1

( i x ) FEATURE:
    ( A ) NAME/KEY: CDS
    ( B ) LOCATION: 316..945
    ( D ) OTHER INFORMATION: /label=ORF2

( i x ) FEATURE:
    ( A ) NAME/KEY: CDS
    ( B ) LOCATION: complement (1084..2124)
    ( D ) OTHER INFORMATION: /label=ORF3

( i x ) FEATURE:
    ( A ) NAME/KEY: CDS
    ( B ) LOCATION: complement (2322..3170)
    ( D ) OTHER INFORMATION: /label=ORF4

( i x ) FEATURE:
    ( A ) NAME/KEY: CDS
    ( B ) LOCATION: 3320..4504
    ( D ) OTHER INFORMATION: /label=ORF5

( x i ) SEQUENCE DESCRIPTION: SEQ ID NO:1:

```
AACAGTTATA TACGCGCATC GGGCCACGTT CCGCCTTCGA GGGCACTTCC GACAGATACG        60
AATTTAAAGA TGGATGAATA ATTAAATTGG AAAGAGTAAC TATATTAATC GAGCGTCATG       120
ACGGCGTCCC GTGAAAATGA GAATTTTCTA CTCGAAACAC CGTGACATTT GACAGACCTG       180
GACTTGTTAT TCTGATATAT AGTGGGTGTG TCTGACCGGC AACATACATA ATGTGCATGC       240
GAAACCACTT TTTCAGTGTA CGCTGACATT GTGCAACACG GAGGGGTAGC ATCTACATAC       300
AATATATGTT GATTAATGAT TGGAGAAAAA ACTATGCAGC TCGCCGATCA TATGGCTAAC       360
TCGCCTTCGC CTATATGGCG GACCCCGCGG GAAAAATCGA CGTACCATCT GATTTACAAC       420
ACCAGTAATG AACATGTCGC ATCCCTGCCC AGATCTGTGC GCCCATTGGC GCGTATCGTT       480
GTGAATGCCG CCGAAACACT TCAGGTCGGT ATGAGAGCCG GGAGGCCGCC ATCAGCAGGA       540
GTTTGGCGAG AGGTGTTTGA TAGAATGATG ACAGCCTTCC GTGACTACGA GCCTACTGCG       600
ACATTTAATG CTGCAGATCC CATTAGAAAA ATGGTCGAGA CAGTTCTACA GAATAATGAA       660
GAGCCTCCGC GGACGCATGC TGAAATGGGT AATCGCCTTA TGAACATTAT GTACTGGTGT       720
```

-continued

| | | | | | |
|---|---|---|---|---|---|
| TGCTTGGGAC | ACGCAGGACA | ATGCTCGATC | TGGCAGTTGT | ACGAGACGAA | TCAGGCCATT | 780 |
| TTAAGTTTAT | TAGATGAAGT | GGTTATCGGC | ACAACAAATC | CCTTTTGCAC | CCTCGAGCAA | 840 |
| TACTGGAAGC | CATTATGCAC | CGCAATCGCC | AACAAGGGGA | CCTCATCGCT | TGTTGAGGAT | 900 |
| GCCAAAGTGG | CCGAGTACCT | GGTTAGCATG | CGCAAATTGA | TATAACACAG | GCACGCTCTG | 960 |
| ATGTTACAGA | CCACAATACC | GCATACATTT | ATTGTAAGGT | TGTTAATAAA | GGTTTATTCT | 1020 |
| ATGTAAGACT | ACAATACTTT | TGACATTGCT | TGTATACATA | TTAAATACTT | TCTCAAGTTC | 1080 |
| CTATTACATA | AAATGGGATC | TATCATTACA | TTCGTTAAGA | GTCTGGATAA | TTTTACTGTT | 1140 |
| TGCCAGCTTC | GATCTTGGAA | CGTACTGTGG | ATAGTGCCTT | ACTTGGAATC | GTGAAAATTT | 1200 |
| GAAGCGTTCA | TTATTTGGAT | ATCTTCCGGT | TGTCCCATAT | CCCGCCCTGG | TACCGCTCGG | 1260 |
| ATACCTTGCC | CGTATGGATT | CGTATTGACA | GTCGCGCAAT | TGGGGACCAA | CAACGCGTGG | 1320 |
| GTCCACACTC | ATTCGGAAAT | TTTCCGATGA | TTCTGAATAT | TTATTGCCGC | TCGTTACGAG | 1380 |
| TTGTTGGACA | TATCTGTAAT | ACAGTTCTTC | TTCTGAAGGA | TCGCTGCACA | TTTGATCTAT | 1440 |
| ACATTGGCCA | GGATGTTCAA | GTCTCAGATG | TTGCATTCTG | GCACAGCACA | ACTTTATGGC | 1500 |
| ATTTCCGACG | TAATCGTCCG | GCAGCCCTGG | GGGAGTTCTA | TATTCGCATA | TTGGGATGGT | 1560 |
| AAGGACAATA | GCAGATCTCG | CAACCTCCAG | GGAGGCTATA | ATAACGTTTT | TAAAGGATGG | 1620 |
| ACTTCTCATA | AAAATCTGTC | GCAAATTACA | CTGAGAATAT | CCTTACTAG | CGCCGATTGA | 1680 |
| GAGCATCGTC | GTCCAATTTT | CTAAATGGAA | AGAAAACAAG | GCGGGCAAGA | GTGTTCCAAA | 1740 |
| CATTTCATT | TTCGACGAAT | CTCTCAAATC | CCATGGCGTG | CAATTGATTG | CAAAATTGGC | 1800 |
| ACTTCCGTTC | ACGTTTGTAT | CTCCAAACTC | TAAGATACTT | TTAATTGAAA | AACTACGTTC | 1860 |
| TAGTGTGGAA | AGAAACCTAT | AGGCAGACCA | TAGAACTATT | TGACACCACA | TATCTTTTTG | 1920 |
| TATGTCAAAC | TGACCATGAT | CGCATGTTGC | TGAATGCACT | AGGGCAATTC | GCTCGCGCGA | 1980 |
| CTCCATACAT | TGAATAATTC | CACACGTCAG | CTCATCTGTT | AGCAAGGTCC | AGTAGTTGAA | 2040 |
| GTCATTTATT | TTTCCCCGCG | GCTGGCCAAA | TCTACCTCTG | GAATATCCA | AGTTGTCGAA | 2100 |
| TATGATCGCA | CCGGCTCTGG | TCATGGTGAA | GGAACTTGTA | GCATAAAGAC | GCAGGTATCA | 2160 |
| TAGGGGTAAT | ATTTTTTATT | CACTCACATG | CAAAAAGTAA | CGCATATTAG | CACCATGTAT | 2220 |
| GGGCCATCAA | TTGACATTTG | CGTAGCACTA | CATCACGATT | ATGTACAACA | TAATGGGACA | 2280 |
| ACAAATGGCA | AGTAGATGCA | ATTTCCTCAC | ACTAGTTGGG | TTTATCTACT | ATTGAATTTT | 2340 |
| CCCCTATCTG | TGATACACTT | GGGAGCCTCT | ACAAGCATAT | TGCCATCATG | TACGTTTTA | 2400 |
| TCTACTGTCT | TAACGCCCAT | GGGAACGGAG | GCGTCGTCGT | CATGTATTGG | ACGGCAACAT | 2460 |
| AGGCAGCAAC | ACAAATTGCG | TTTAGGTGGG | GTGCATGTGG | ACTCGATACC | AAGACCCTGC | 2520 |
| AGCTGGGGAA | CGTCTGGTGG | AGAGCCGATA | ATTTGATATA | CGCACGCCAT | ATTACTATCG | 2580 |
| TTGAAGTACG | CCTTATCTTC | TATGTTTTCA | AATTTAGGTT | CCCAAGTGGA | CGTGAGAAGT | 2640 |
| GTTTGTATCT | CACATGGAAG | GGCCCAAGGC | ATTCCAGCCC | AGGTGCCTGG | TACTTTAATG | 2700 |
| GCAAACAAAC | GTTTTGGTAG | AGGTATTGAT | TCTATTGCAG | TTCTGCAGAT | ATCTGCAGCT | 2760 |
| CCGAGTATCC | ACAGGCTATA | CGATACGTTA | TCGGAGGCCT | CCGATTCTAG | CATTACATAG | 2820 |
| CCGGTCAGTA | GATCCTGCCA | TTCGGTAGCG | CAACCGGCTA | CATCTTCAAA | CAGTCTCACA | 2880 |
| ATAAATGCAT | CTCTCGTTCC | TGCCAATCCG | GAACCGGGCA | TACCACTCCC | ACCTGCCGAT | 2940 |
| TTAATTCTCA | CAATTGGGCG | ATGCCGGCGG | GGCAAAACGA | ATGTGGATTT | GGCAAACCGA | 3000 |
| CACAGGTCTG | CTGTACGGAC | TAATATGGGC | ACACCCACAT | CATTCTTCAG | ATGCTCCATG | 3060 |
| CATTGTTCTA | TGAGAAAGAT | CCATAGGGTG | GAGGCAGCGT | CACGAGATCG | CCCAGGCAAT | 3120 |
| CGATCGCATT | CGTCTAGTAA | AGTGACGAGA | GTTATCATGC | ACACACCCAT | GCCCACGCCT | 3180 |

| | | | | | |
|---|---|---|---|---|---|
| TCCGAATAAC | TGGAGCTGTG | GAAGATCGGA | AACGTCTTTT | TGACTGCCGG | TCTCGTACTA | 3240
| CTTTCGCACA | GGTGTATACC | CGGACGCGTA | CTATATATTT | TATATCATTC | AACGTCCCGA | 3300
| AATTACATAC | GTGGCGGCGA | TGGAAGTAGA | TGTTGAGTCT | TCGAAAGTAA | GTGCCTCGAA | 3360
| TATGGGTATT | GTCTGTGAAA | ATATCGAAAG | CGGTACGACG | GTTGCAGAAC | CGTCGATGTC | 3420
| GCCAGATACT | AGTAACAATA | GCTTCGATAA | CGAAGACTTC | CGTGGGCCTG | AATACGATGT | 3480
| GGAGATAAAT | ACCAGAAAAT | CTGCTAATCT | TGATCGTATG | AATCTTCGT | GCCGTGAACA | 3540
| ACGAGCGGCG | TGCGAACTTC | GAAAGTGTTC | GTGTCCTACG | TCTGCCGTGC | GCATGCAATA | 3600
| CAGTATTCTT | TCATCTCTCG | CTCCGGGTTC | AGAGGGTCAT | GTATATATAT | GTACTAGATA | 3660
| CGGGGACGCG | GACCAAAAAA | AATGCATAGT | GAAGGCAGTC | GTTGGAGGAA | AGAATCCCGG | 3720
| GAGGGAAGTG | GATATTTTAA | AAACCATCTC | ACATAAATCA | ATTATAAAAT | TAATCCATGC | 3780
| CTATAAATGG | AAAAATGTTG | TGTGTATGGC | AATGCGTGTA | TATCGTTATG | ATCTTTTCAC | 3840
| ATATATTGAC | GGAGTCGGCC | CTATGCCCCT | TCAACAGATG | ATCTATATTC | AACGTGGACT | 3900
| ACTAGAGGCG | CTAGCATACA | TACATGAAAG | GGGCATCATT | CACCGAGACG | TAAAGACGGA | 3960
| GAATATATTC | TTGGATAATC | ACGAAAATGC | AGTTTGGGT | GACTTCGGTG | CTGCATGTCA | 4020
| ACTAGGAGAT | TGTATAGATA | CGCCCCAATG | TTACGGTTGG | AGCGGAACTG | TGGAAACAAA | 4080
| TTCGCCGGAA | TTATCTGCAC | TTGATCCGTA | TTGCACAAAA | ACAGATATTT | GGAGTGCCGG | 4140
| ATTGGTTCTA | TATGAGATGG | CAATTAAAAA | TGTACCATTG | TTTAGTAAGC | AGGTGAAAAG | 4200
| TTCGGGATCT | CAGCTGAGAT | CCATAATACG | GTGCATGCAA | GTGCATGAAC | TGGAGTTTCC | 4260
| CCGCAACGAT | TCTACCAACC | TCTGTAAACA | TTTCAAACAA | TATGCGGTTC | GTGTACGACC | 4320
| GCCTTATACC | ATTCCTCGAG | TTATAAGAAA | TGGGGGGATG | CCAATGGATG | TTGAATATGT | 4380
| CATTTCTAAA | ATGCTTACGT | TTGACCAGGA | GTTCAGACCT | TCTGCTAAGG | AAATATTGAA | 4440
| TATGCCCCTA | TTTACTAAGG | CGCCGATTAA | CCTGCTTAAT | ATCACACCCT | CTGACAGTGT | 4500
| CTAACGGTAT | ACAGGCGGGA | GCGGGTA | | | | 4527

(2) INFORMATION FOR SEQ ID NO:2:

(i) SEQUENCE CHARACTERISTICS:
        (A) LENGTH: 209 amino acids
        (B) TYPE: amino acid
        (D) TOPOLOGY: linear (ii) MOLECULE TYPE: protein (ix) FEATURE: ORF-2

(xi) SEQUENCE DESCRIPTION: SEQ ID NO:2:

```
Met Ile Gly Glu Lys Thr Met Gln Leu Ala Asp His Met Ala Asn Ser
 1               5                  10                  15

Pro Ser Pro Ile Trp Arg Thr Pro Arg Glu Lys Ser Thr Tyr His Leu
            20                  25                  30

Ile Tyr Asn Thr Ser Asn Glu His Val Ala Ser Leu Pro Arg Ser Val
        35                  40                  45

Arg Pro Leu Ala Arg Ile Val Val Asn Ala Ala Glu Thr Leu Gln Val
    50                  55                  60

Gly Met Arg Ala Gly Arg Pro Pro Ser Ala Gly Val Trp Arg Glu Val
65                  70                  75                  80

Phe Asp Arg Met Met Thr Ala Phe Arg Asp Tyr Glu Pro Thr Ala Thr
                85                  90                  95

Phe Asn Ala Ala Asp Pro Ile Arg Lys Met Val Glu Thr Val Leu Gln
            100                 105                 110

Asn Asn Glu Glu Pro Pro Arg Thr His Ala Glu Met Gly Asn Arg Leu
        115                 120                 125
```

```
Met  Asn  Ile  Met  Tyr  Trp  Cys  Cys  Leu  Gly  His  Ala  Gly  Gln  Cys  Ser
     130                 135                      140

Ile  Trp  Gln  Leu  Tyr  Glu  Thr  Asn  Gln  Ala  Ile  Leu  Ser  Leu  Leu  Asp
145                      150                      155                      160

Glu  Val  Val  Ile  Gly  Thr  Thr  Asn  Pro  Phe  Cys  Thr  Leu  Glu  Gln  Tyr
                    165                      170                      175

Trp  Lys  Pro  Leu  Cys  Thr  Ala  Ile  Ala  Asn  Lys  Gly  Thr  Ser  Ser  Leu
               180                      185                      190

Val  Glu  Asp  Ala  Lys  Val  Ala  Glu  Tyr  Leu  Val  Ser  Met  Arg  Lys  Leu
          195                      200                      205
Ile
209
```

( 2 ) INFORMATION FOR SEQ ID NO:3:

( i ) SEQUENCE CHARACTERISTICS:
        ( A ) LENGTH: 346 amino acids
        ( B ) TYPE: amino acid
        ( D ) TOPOLOGY: linear ( i i ) MOLECULE TYPE: protein ( i x ) FEATURE: ORF-3

( x i ) SEQUENCE DESCRIPTION: SEQ ID NO:3:

```
Met  Thr  Arg  Ala  Gly  Ala  Ile  Ile  Phe  Asp  Asn  Leu  Asp  Ile  Pro  Arg
 1                  5                   10                      15

Gly  Arg  Phe  Gly  Gln  Pro  Arg  Gly  Lys  Ile  Asn  Asp  Phe  Asn  Tyr  Trp
               20                      25                      30

Thr  Leu  Leu  Thr  Asp  Glu  Leu  Thr  Cys  Gly  Ile  Ile  Gln  Cys  Met  Glu
          35                      40                      45

Ser  Arg  Glu  Arg  Ile  Ala  Leu  Val  His  Ser  Ala  Thr  Cys  Asp  His  Gly
     50                      55                      60

Gln  Phe  Asp  Ile  Gln  Lys  Asp  Met  Trp  Cys  Gln  Ile  Val  Leu  Trp  Ser
65                       70                      75                       80

Ala  Tyr  Arg  Phe  Leu  Ser  Thr  Leu  Glu  Arg  Ser  Phe  Ser  Ile  Lys  Ser
               85                      90                      95

Ile  Leu  Glu  Phe  Gly  Asp  Thr  Asn  Val  Asn  Gly  Ser  Ala  Asn  Phe  Ala
               100                     105                     110

Ile  Asn  Cys  Thr  Pro  Trp  Asp  Leu  Arg  Asp  Ser  Ser  Lys  Met  Lys  Met
          115                     120                     125

Phe  Gly  Thr  Leu  Leu  Pro  Ala  Leu  Phe  Ser  Phe  His  Leu  Glu  Asn  Trp
     130                     135                     140

Thr  Thr  Met  Leu  Ser  Ile  Gly  Ala  Ser  Lys  Gly  Tyr  Ser  Gln  Cys  Asn
145                      150                     155                      160

Leu  Arg  Gln  Ile  Phe  Met  Arg  Ser  Pro  Ser  Phe  Lys  Asn  Val  Ile  Ile
               165                     170                     175

Ala  Ser  Leu  Glu  Val  Ala  Arg  Ser  Ala  Ile  Val  Leu  Thr  Ile  Pro  Ile
               180                     185                     190

Cys  Glu  Tyr  Arg  Thr  Pro  Pro  Gly  Leu  Pro  Asp  Asp  Tyr  Val  Gly  Asn
               195                     200                     205

Ala  Ile  Lys  Leu  Cys  Cys  Ala  Arg  Met  Gln  His  Leu  Arg  Leu  Glu  His
     210                     215                     220

Pro  Gly  Gln  Cys  Ile  Asp  Gln  Met  Cys  Ser  Asp  Pro  Ser  Glu  Glu  Glu
225                      230                     235                      240

Leu  Tyr  Tyr  Arg  Tyr  Val  Gln  Gln  Leu  Val  Thr  Ser  Gly  Asn  Lys  Tyr
               245                     250                     255

Ser  Glu  Ser  Ser  Glu  Asn  Phe  Arg  Met  Ser  Val  Asp  Pro  Arg  Val  Val
               260                     265                     270
```

```
Gly Pro Gln Leu Arg Asp Cys Gln Tyr Glu Ser Ile Arg Ala Arg Tyr
            275                 280                 285

Pro Ser Gly Thr Arg Ala Gly Tyr Gly Thr Thr Gly Arg Tyr Pro Asn
        290                 295                 300

Asn Glu Arg Phe Lys Phe Ser Arg Phe Gln Val Arg His Tyr Pro Gln
305                 310                 315                 320

Tyr Val Pro Arg Ser Lys Leu Ala Asn Ser Lys Ile Ile Gln Thr Leu
                325                 330                 335

Asn Glu Cys Asn Asp Arg Ser His Phe Met
            340                 345
```

( 2 ) INFORMATION FOR SEQ ID NO:4:

( i ) SEQUENCE CHARACTERISTICS:
        ( A ) LENGTH: 282 amino acids
        ( B ) TYPE: amino acid
        ( D ) TOPOLOGY: linear
    ( i i ) MOLECULE TYPE: protein ( i x ) FEATURE: ORF-4

( x i ) SEQUENCE DESCRIPTION: SEQ ID NO:4:

```
Met Gly Val Cys Met Ile Thr Leu Val Thr Leu Leu Asp Glu Cys Asp
 1               5                  10                  15

Arg Leu Pro Gly Arg Ser Arg Asp Ala Ala Ser Thr Leu Trp Ile Phe
            20                  25                  30

Leu Ile Glu Gln Cys Met Glu His Leu Lys Asn Asp Val Gly Val Pro
            35                  40                  45

Ile Leu Val Arg Thr Ala Asp Leu Cys Arg Phe Ala Lys Ser Thr Phe
        50                  55                  60

Val Leu Pro Arg Arg His Arg Pro Ile Val Arg Ile Lys Ser Ala Gly
65                  70                  75                  80

Gly Ser Gly Met Pro Gly Ser Gly Leu Ala Gly Thr Arg Asp Ala Phe
                85                  90                  95

Ile Val Arg Leu Phe Glu Asp Val Ala Gly Cys Ala Thr Glu Trp Gln
            100                 105                 110

Asp Leu Leu Thr Gly Tyr Val Met Leu Glu Ser Glu Ala Ser Asp Asn
            115                 120                 125

Val Ser Tyr Ser Leu Trp Ile Leu Gly Ala Ala Asp Ile Cys Arg Thr
130                 135                 140

Ala Ile Glu Ser Ile Pro Leu Pro Lys Arg Leu Phe Ala Ile Lys Val
145                 150                 155                 160

Pro Gly Thr Trp Ala Gly Met Pro Trp Ala Leu Pro Cys Glu Ile Gln
                165                 170                 175

Thr Leu Leu Thr Ser Thr Trp Glu Pro Lys Phe Glu Asn Ile Glu Asp
            180                 185                 190

Lys Ala Tyr Phe Asn Asp Ser Asn Met Ala Cys Val Tyr Gln Ile Ile
            195                 200                 205

Gly Ser Pro Pro Asp Val Pro Gln Leu Gln Gly Leu Gly Ile Glu Ser
        210                 215                 220

Thr Cys Thr Pro Pro Lys Arg Asn Leu Cys Cys Cys Leu Cys Cys Arg
225                 230                 235                 240

Pro Ile His Asp Asp Asp Ala Ser Val Pro Met Gly Val Lys Thr Val
                245                 250                 255

Asp Lys Asn Val His Asp Gly Asn Met Leu Val Glu Ala Pro Lys Cys
            260                 265                 270

Ile Thr Asp Arg Gly Lys Phe Asn Ser Arg
            275                 280
```

( 2 ) INFORMATION FOR SEQ ID NO:5:

( i ) SEQUENCE CHARACTERISTICS:
        ( A ) LENGTH: 394 amino acids
        ( B ) TYPE: amino acid
        ( D ) TOPOLOGY: linear ( i i ) MOLECULE TYPE: protein ( i x ) FEATURE: ORF-5

( x i ) SEQUENCE DESCRIPTION: SEQ ID NO:5:

```
Met Glu Val Asp Val Glu Ser Ser Lys Val Ser Ala Ser Asn Met Gly
 1               5                  10                  15

Ile Val Cys Glu Asn Ile Glu Ser Gly Thr Thr Val Ala Glu Pro Ser
                20                  25                  30

Met Ser Pro Asp Thr Ser Asn Asn Ser Phe Asp Asn Glu Asp Phe Arg
            35                  40                  45

Gly Pro Glu Tyr Asp Val Glu Ile Asn Thr Arg Lys Ser Ala Asn Leu
        50                  55                  60

Asp Arg Met Glu Ser Ser Cys Arg Glu Gln Arg Ala Ala Cys Glu Leu
 65                  70                  75                  80

Arg Lys Cys Ser Cys Pro Thr Ser Ala Val Arg Met Gln Tyr Ser Ile
                85                  90                  95

Leu Ser Ser Leu Ala Pro Gly Ser Glu Gly His Val Tyr Ile Cys Thr
                100                 105                 110

Arg Tyr Gly Asp Ala Asp Gln Lys Lys Cys Ile Val Lys Ala Val Val
            115                 120                 125

Gly Gly Lys Asn Pro Gly Arg Glu Val Asp Ile Leu Lys Thr Ile Ser
        130                 135                 140

His Lys Ser Ile Ile Lys Leu Ile His Ala Tyr Lys Trp Lys Asn Val
145                 150                 155                 160

Val Cys Met Ala Met Arg Val Tyr Arg Tyr Asp Leu Phe Thr Tyr Ile
                165                 170                 175

Asp Gly Val Gly Pro Met Pro Leu Gln Gln Met Ile Tyr Ile Gln Arg
            180                 185                 190

Gly Leu Leu Glu Ala Leu Ala Tyr Ile His Glu Arg Gly Ile Ile His
        195                 200                 205

Arg Asp Val Lys Thr Glu Asn Ile Phe Leu Asp Asn His Glu Asn Ala
    210                 215                 220

Val Leu Gly Asp Phe Gly Ala Ala Cys Gln Leu Gly Asp Cys Ile Asp
225                 230                 235                 240

Thr Pro Gln Cys Tyr Gly Trp Ser Gly Thr Val Glu Thr Asn Ser Pro
                245                 250                 255

Glu Leu Ser Ala Leu Asp Pro Tyr Cys Thr Lys Thr Asp Ile Trp Ser
            260                 265                 270

Ala Gly Leu Val Leu Tyr Glu Met Ala Ile Lys Asn Val Pro Leu Phe
        275                 280                 285

Ser Lys Gln Val Lys Ser Ser Gly Ser Gln Leu Arg Ser Ile Ile Arg
    290                 295                 300

Cys Met Gln Val His Glu Leu Glu Phe Pro Arg Asn Asp Ser Thr Asn
305                 310                 315                 320

Leu Cys Lys His Phe Lys Gln Tyr Ala Val Arg Val Arg Pro Pro Tyr
                325                 330                 335

Thr Ile Pro Arg Val Ile Arg Asn Gly Gly Met Pro Met Asp Val Glu
            340                 345                 350

Tyr Val Ile Ser Lys Met Leu Thr Phe Asp Gln Glu Phe Arg Pro Ser
```

|     |     |     |     |     |     |     |     |     |     |     |     |
|-----|-----|-----|-----|-----|-----|-----|-----|-----|-----|-----|-----|
|     | 355 |     |     |     | 360 |     |     |     | 365 |     |     |
| Ala | Lys | Glu | Ile | Leu | Asn | Met | Pro | Leu | Phe | Thr | Lys | Ala | Pro | Ile | Asn |
|     | 370 |     |     |     | 375 |     |     |     | 380 |     |     |
| Leu | Leu | Asn | Ile | Thr | Pro | Ser | Asp | Ser | Val |
|     | 385 |     |     |     | 390 |

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGATCCGTCG ACCATG        16

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AATTCCCCCC CCCCC        15

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTAGGTGGTC TGAAGGCACT TTGGTAGTAG TA        32

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TACCTACTAA TTTACCACCA GAAACTACAA ACTGCTG        37

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TGGATCATTA AACAGACTTT TAGGTCTGT ATTGTT        36

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (x i) SEQUENCE DESCRIPTION: SEQ ID NO:11:

GGCAGGCCTC TTGCGGCTGC AGGGATTGTG GTAACAGG    38

(2) INFORMATION FOR SEQ ID NO:12:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (x i) SEQUENCE DESCRIPTION: SEQ ID NO:12:

GCAAAAGGCG CAACAGAAGA CCTTGTTGTG GCTTGGC    37

(2) INFORMATION FOR SEQ ID NO:13:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (x i) SEQUENCE DESCRIPTION: SEQ ID NO:13:

GAAAGAGAGG CGAAGAATAC ATGGCGCTTG GTATTCCGG    39

(2) INFORMATION FOR SEQ ID NO:14:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:14:

GAAATATCTA ATACTCTCTT CGGGGAATTC AGGATCGT    38

(2) INFORMATION FOR SEQ ID NO:15:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (x i) SEQUENCE DESCRIPTION: SEQ ID NO:15:

GTCGACGGAT CCCATG    16